(12) United States Patent
Inoue et al.

(10) Patent No.: US 10,539,509 B2
(45) Date of Patent: Jan. 21, 2020

(54) DISPLAY SYSTEM, DISPLAY DEVICE, DISPLAY METHOD, AND NON-TRANSITORY COMPUTER READABLE RECORDING MEDIUM

(71) Applicant: NS SOLUTIONS CORPORATION, Tokyo (JP)

(72) Inventors: Kazuyoshi Inoue, Tokyo (JP); Yoichiro Sumito, Tokyo (JP)

(73) Assignee: NS SOLUTIONS CORPORATION, Tokyo (JP)

( * ) Notice: Subject to any disclaimer, the term of this patent is extended or adjusted under 35 U.S.C. 154(b) by 44 days.

(21) Appl. No.: 15/753,119

(22) PCT Filed: Jun. 27, 2016

(86) PCT No.: PCT/JP2016/069055
§ 371 (c)(1),
(2) Date: Feb. 15, 2018

(87) PCT Pub. No.: WO2017/033561
PCT Pub. Date: Mar. 2, 2017

(65) Prior Publication Data
US 2018/0238810 A1   Aug. 23, 2018

(30) Foreign Application Priority Data
Aug. 21, 2015   (JP) ................................. 2015-163825

(51) Int. Cl.
*G06K 9/00* (2006.01)
*G01N 21/84* (2006.01)
(Continued)

(52) U.S. Cl.
CPC ........... *G01N 21/84* (2013.01); *G05B 19/418* (2013.01); *G06F 1/163* (2013.01); *G06F 3/011* (2013.01);
(Continued)

(58) Field of Classification Search
None
See application file for complete search history.

(56) References Cited

U.S. PATENT DOCUMENTS

2009/0141964 A1   6/2009 Magara
2013/0120449 A1   5/2013 Ihara et al.
(Continued)

FOREIGN PATENT DOCUMENTS

JP   2000-230806 A   8/2000
JP   2003-338700 A   11/2003
(Continued)

OTHER PUBLICATIONS

International Preliminary Report on Patentability of related International Patent Application No. PCT/JP2016/069055 dated Mar. 8, 2018.
(Continued)

*Primary Examiner* — Stephen P Coleman
(74) *Attorney, Agent, or Firm* — Arent Fox LLP

(57) ABSTRACT

A display system which has: a display device configured to be able to display an image superimposed on a reality space; and a managing device configured to manage the image the display device displays, wherein the display device has a display processor configured to read at least one of a qualified image and a disqualified image for an inspection target existing in the reality space from a memory and to display the read image superimposed on the reality space seen through an optical see-through displayer, on the displayer.

11 Claims, 5 Drawing Sheets

(51) Int. Cl.
*G05B 19/418* (2006.01)
*G06F 1/16* (2006.01)
*G06F 3/14* (2006.01)
*G09G 5/377* (2006.01)
*G06F 3/01* (2006.01)

(52) U.S. Cl.
CPC .............. *G06F 3/14* (2013.01); *G09G 5/377* (2013.01); *G05B 2219/32014* (2013.01); *G05B 2219/35482* (2013.01); *G05B 2219/39449* (2013.01); *Y02P 90/14* (2015.11)

(56) References Cited

U.S. PATENT DOCUMENTS

| | | | | |
|---|---|---|---|---|
| 2014/0313334 | A1* | 10/2014 | Slotky | H04N 5/23222 348/148 |
| 2016/0004306 | A1* | 1/2016 | Maltz | G06F 3/013 345/173 |
| 2016/0050351 | A1* | 2/2016 | Lee | H04N 5/2252 348/221.1 |

FOREIGN PATENT DOCUMENTS

| | | |
|---|---|---|
| JP | 2004-184095 A | 7/2004 |
| JP | 2004-279037 A | 10/2004 |
| JP | 2005-142552 A | 6/2005 |
| JP | 2007-309729 A | 6/2005 |
| JP | 2009-150866 A | 7/2009 |
| JP | 2010-026757 A | 2/2010 |
| JP | 2011-248860 A | 12/2011 |
| JP | 2012-007985 A | 1/2012 |
| JP | 2015-001468 A | 1/2015 |

OTHER PUBLICATIONS

International Search Report of related international Patent Application No. PCT/JP2016/069055 dated Aug. 9, 2016.

Japanese Office Action of related Japanese Patent Application No. 2017-119626 dated Aug. 22, 2017.

* cited by examiner

| ITEM | REFERENCE IMAGE ||
|---|---|---|
| | QUALIFIED IMAGE | DISQUALIFIED IMAGE |
| A001 | P1001,P1004,··· | P1009,P1052,··· |
| A002 | P1921,P1321,··· | P1292,P3211,··· |
| ⋮ | ⋮ | ⋮ |

118

DISPLAY SYSTEM, DISPLAY DEVICE, DISPLAY METHOD, AND NON-TRANSITORY COMPUTER READABLE RECORDING MEDIUM

CROSS-REFERENCE TO RELATED APPLICATIONS

This application is a National Stage entry of International Application No. PCT/JP20161069055, filed on Jun. 27, 2016, which claims priority to Japanese Patent Application No. 2015-163825, filed on Aug. 21, 2015. The disclosures of the priority applications are incorporated in their entirety herein by reference.

TECHNICAL FIELD

The present invention relates to a display system, a display device, a display method, and a non-transitory computer readable recording medium.

BACKGROUND ART

A plurality of inspection processes are conventionally performed in an automobile manufacturing plant or the like, and a managing system which manages each inspection process is known. Patent Literature 1 discloses a system which displays to that effect when an inspection result of an inspection process having been performed does not satisfy a predetermined standard. Further, the inspection processes include a visual inspection by an inspector. In the visual inspection, the inspector judges whether an inspection target is qualified or disqualified, in accordance with a criterion predetermined for each inspection item.

Meanwhile, an operation support technology using an augmented reality (hereinafter, AR) technology is known in recent years. As a technology for operation support, Patent Literature 2 discloses a technology to display information related to a fault recovery operation superimposed on a video picture of a reality space in a wearable AR display device worn by an operator.

CITATION LIST

Patent Literature

Patent Literature 1: Japanese Laid-open Patent Publication No. 2010-26757
Patent Literature 2: Japanese Laid-open Patent Publication No. 2011-248860

SUMMARY OF INVENTION

Technical Problem

However, a visual inspection by an operator may cause misjudgment, and there is a problem that a product which should be judged as disqualified is shipped.

The present invention is made in view of the above problem, and its object is to perform support leading to improvement of an inspection accuracy of a visual inspection by an inspector.

Solution to Problem

Thus, the present invention is a display system which has: a display device configured to be able to display an image superimposed on a reality space; and a managing device configured to manage the image the display device displays, wherein the display device has: a first acceptor configured to accept at least one of a qualified image and a disqualified image for an inspection target existing in the reality space, from a memory; and a display processor configured to display the read image superimposed on the reality space seen through an optical see-through displayer, on the displayer.

Advantageous Effects of Invention

According to the present invention, it is possible to improve an inspection accuracy in an inspection process which includes a visual inspection by an inspector.

DESCRIPTION OF EMBODIMENTS

Hereinafter, embodiments of the present invention will be described based on the drawings.

Figure 1:
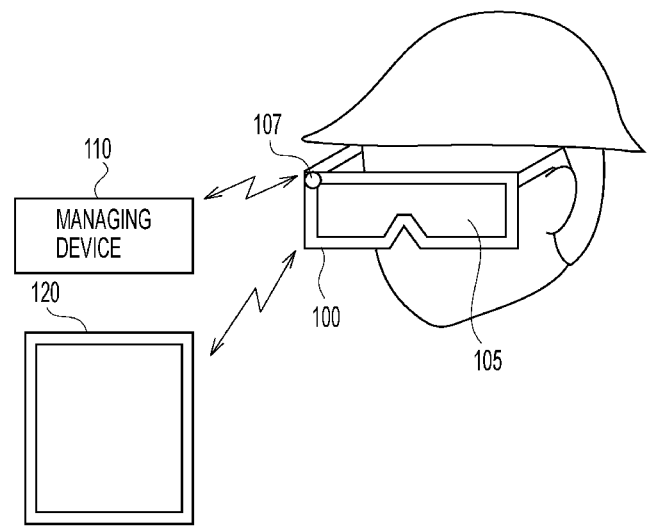
FIG. 1 is a diagram illustrating an AR display system.

FIG. 1 is a diagram illustrating an augmented reality display system as a display system. Hereinafter, the augmented reality display system is referred to as an AR display system. The AR display system has an AR display device 100, a managing device 110, and a PC 120.

The AR display device 100 is a glass-type device. In this embodiment, an inspector performs a visual inspection of an inspection target, wearing the AR display device 100, in a final inspection of a finished car in an automobile plant. The AR display device 100 is also an optical see-through displayer, which is provided with an optical see-through display unit 105 at a position corresponding to a lens part of glasses. The inspector wearing the AR display device 100 can see an object which exists ahead of a line of sight, in a reality space, via the display unit 105 of the AR display device 100. Further, since an arbitrary image is displayed on the display unit 105, the inspector wearing the AR display device 100 can recognize a state where the arbitrary image is superimposed on the reality space viewed through the display unit 105. As described above, the AR display device 100 is a display device capable of displaying an image superimposed on a reality space. Note that a space in which a reality space and an arbitrary image are combined is referred to an augmented reality space. Further, a photographing unit 107 is provided at a position adjacent to the display unit 105. The photographing unit 107 is provided in a manner that a sight line direction of a wearer of the AR display device 100 coincides with a photographing direction of the photographing unit 107. Thereby, the photographing unit 107 can photograph an image of the reality space viewed by the inspector wearing the AR display device 100. Note that as another example, the photographing unit 107 may be provided in a manner that the photographing direction and the sight line direction of the wearer have a constant relationship.

The managing device 110 manages information which the AR display device 100 displays. The PC 120 is an information processing device used by a predetermined user such as a supervisor of the inspector, for example. Here, the PC 120 is an example of an external device. The AR display device 100 is capable of communicating with the managing device 110 and the PC 120 via a network. The network between the AR display device 100 and the managing device 110 and the network between the AR display device 100 and the PC 120 may be the same or may be different.

Figure 2:
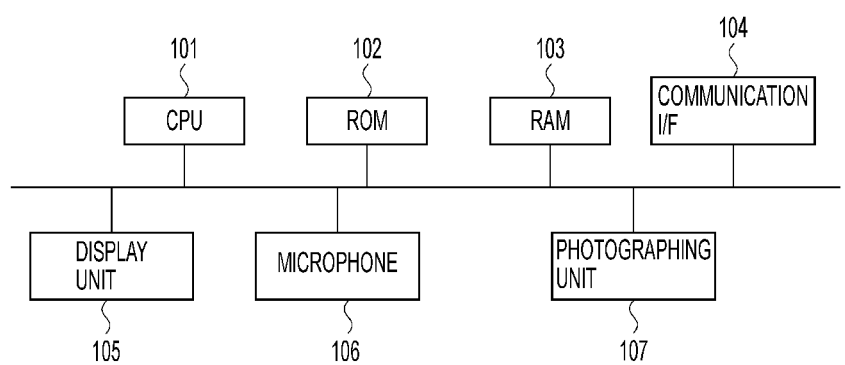
FIG. 2 is a diagram illustrating an AR display device.

FIG. 2 is a diagram illustrating the AR display device 100. The AR display device 100 has a CPU 101, a ROM 102, a RAM 103, a communication I/F 104, the display unit 105, a microphone 106, and the photographing unit 107. The CPU 101 reads a control program stored in the ROM 102 and executes various processings. The RAM 103 is used as a main memory of the CPU 101 and a temporary storage area of a work area or the like. Note that later-described function and processing of the AR display device 100 are enabled by the CPU 101 reading the program stored in the ROM 102 and executing the program.

The communication I/F 104 performs a communication processing with the managing device 110 and the PC 120 via the network. The display unit 105 displays various information. The microphone 106 inputs voice such as speech of the inspector who wears the AR display device 100. Note that the voice is transmitted to the CPU 101 and a voice recognition processing is performed in the CPU 101. The CPU 101 can accept various instructions by a user, from a result of voice recognition. The photographing unit 107 performs photographing of the reality space. Incidentally, in this embodiment, the AR display device 100 accepts the instruction from the user by the voice which is input to the microphone 106, but a user interface to accept the instruction from the user should not be limited to the microphone 106. As another example, the AR display device 100 may accept an instruction corresponding to pressing down of a not-shown button provided in the AR display device 100. Further, as another example, the AR display device 100 may accept an instruction corresponding to a gesture recognition result of a gesture by a user, based on a moving image photographed by the photographing unit 107.

Figure 3:
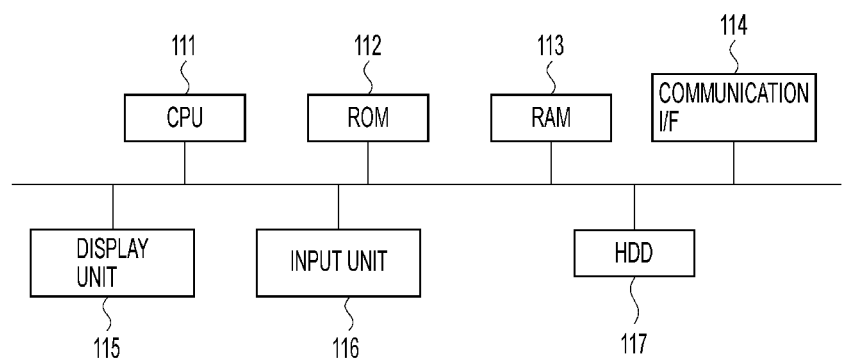
FIG. 3 is a diagram illustrating a managing device.

FIG. 3 is a diagram illustrating the managing device 110. The managing device 110 has a CPU 111, a ROM 112, a RAM 113, a communication I/F 114, a display unit 115, an input unit 116, and an HDD 117. The CPU 111, the ROM 112, the RAM 113, and the communication I/F 114 are similar to the CPU 101, the ROM 102, the RAM 103, and the communication I/F 104, respectively. The display unit 115 displays various information. The input unit 116 has a keyboard or a mouse, and accepts various manipulations by the user. The HDD 117 stores data, various programs, and so on. Later-described function and processing of the managing device 110 are enabled by the CPU 111 reading the program stored in the ROM 112 or the HDD 117 and executing the program. Note that a configuration of the PC 120 is the same as the configuration of the managing device 110.

Figure 4:
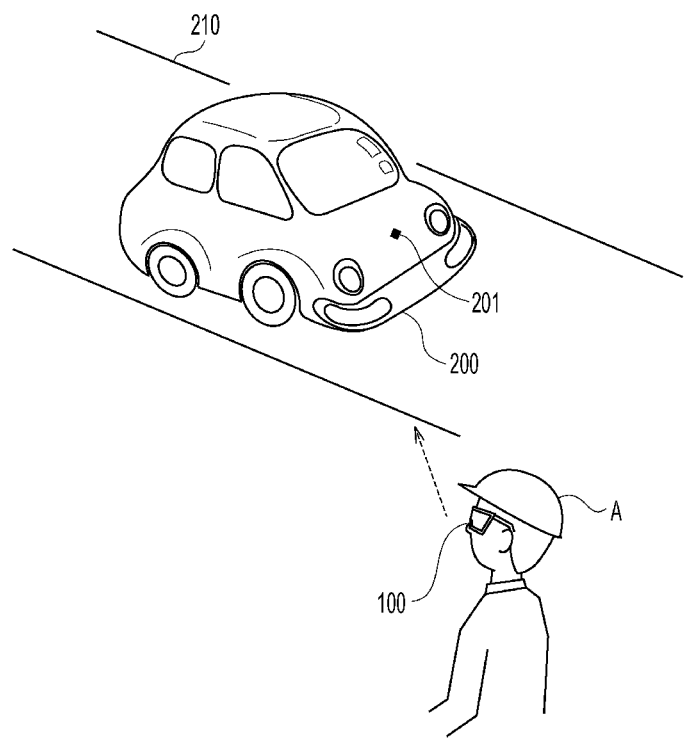
FIG. 4 is an explanatory diagram illustrating a finished car inspection.

FIG. 4 is an explanatory diagram of a finished car inspection performed in an automobile plant. The finished car inspection includes an inspection by an inspection device and a visual inspection by an inspector, and an inspector A wearing the AR display device 100 performs a visual inspection. A finished car 200 is conveyed on a belt conveyor 210 to the front of the inspector A. A specification (vehicle type, model, equipment, color, and so on) of an automobile being an inspection object which is conveyed on the belt conveyor 210 varies, and the inspector A first specifies the specification of the automobile. Then, the inspector specifies an inspection item in correspondence with the specification while referring to a specification sheet describing the inspection item for each specification, checks an inspection target indicated in the inspection item by visual observation, and makes judgment of qualified or disqualified. Hereinafter, the inspection will be described by an example of the inspection of a shape of an emblem 201, with the emblem 201 provided in the front of the finished car 200 being the inspection target.

Figure 5:
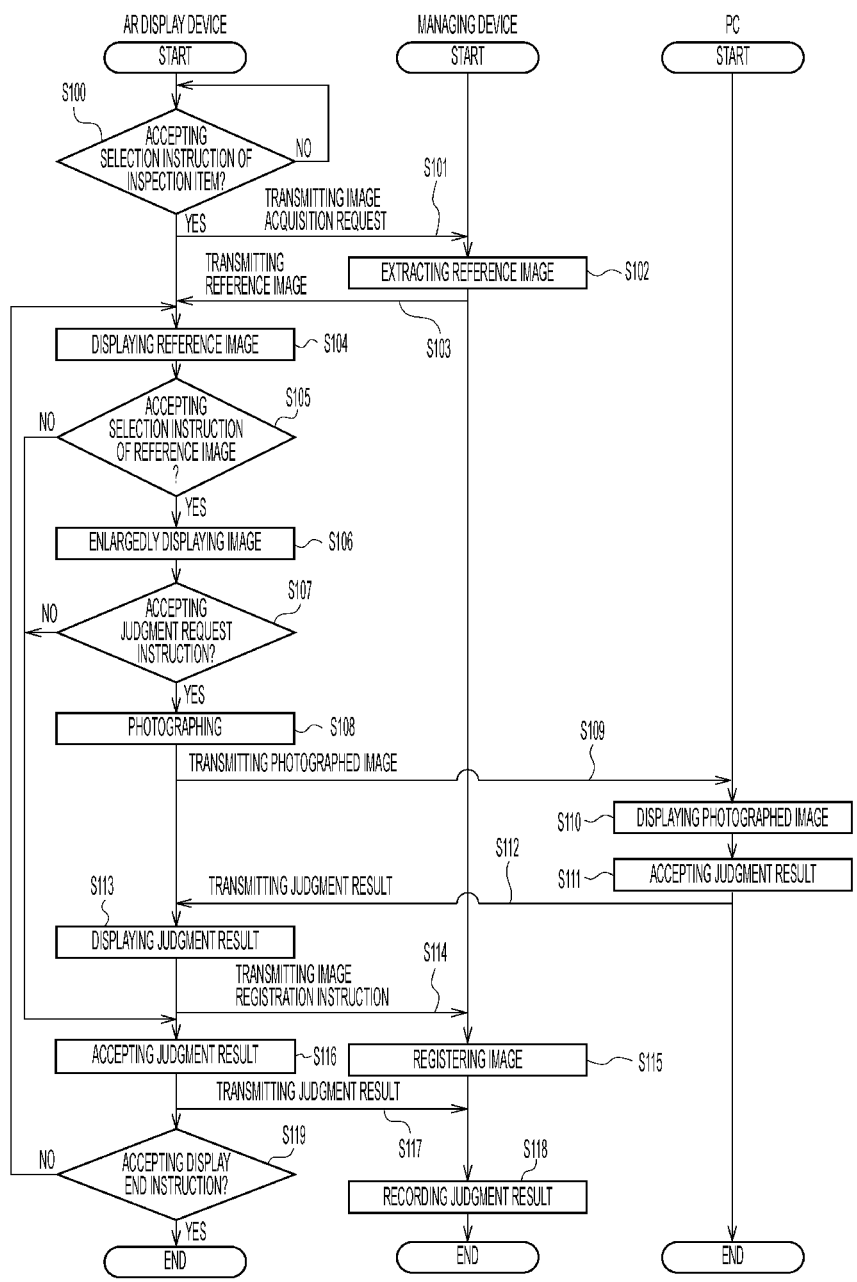
FIG. 5 is a flowchart illustrating an inspection support processing by an AR display system.

FIG. 5 is a flowchart illustrating an inspection support processing by the AR display system. This processing is a processing executed at the time that the inspector wearing the AR display device 100 performs the inspection. First, in S100, in response to speech by the inspector, the CPU 101 of the AR display device 100 confirms whether or not a selection instruction of the inspection item is accepted. Here, the inspection item is information indicating an inspection target which is going to be inspected by the inspector and an inspection content thereof. When the inspector speaks "shape inspection of an emblem", the CPU 101 of the AR display device 100 performs voice recognition to voice having been input from the microphone 106, and in response to a voice recognition result, accepts the selection instruction of the inspection item "shape of emblem". Note that the user interface for the inspector to input the selection instruction should not be limited to the microphone 106, as described above. As another example, a user may perform an input of a selection instruction by pressing down of a button, a gesture, or the like. Note that in the following explanation, also in a case where the inspector inputs various instructions, the user interface for an instruction input should not be limited to the embodiment. Here, the processing of S100 is an example of an accepting processing.

If accepting the selection instruction (Yes in S100), the CPU 101 of the AR display device 100 proceeds the processing to S101. In S101, the CPU 101 of the AR display device 100 transmits an acquisition request of an image which includes the inspection item related to the selection instruction, to the managing device 110 via the communication I/F 104 (transmission processing). When receiving the image acquisition request via the communication I/F 114, the CPU 111 of the managing device 110 proceeds the processing to S102. In S102, the CPU 111 of the managing device 110 extracts a reference image registered in association with the inspection item indicated in the image acquisition request, from a reference image DB. Here, the reference image is an image to be referred to in an inspection, and is an image of an inspection target judged as qualified or disqualified.

Figures 6, 7:
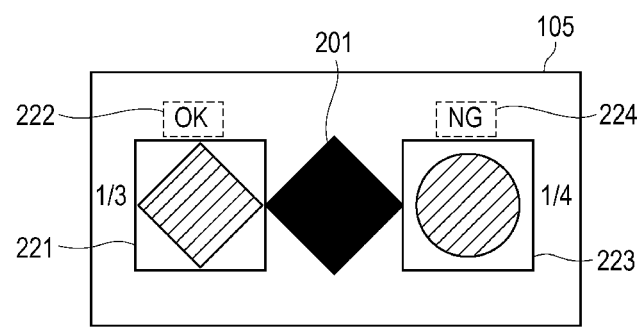
FIG. 6 is a table illustrating an example of a data configuration of a reference image DB.
FIG. 7 is a diagram illustrating a display example of a reference image.

FIG. 6 is a table illustrating an example of a data configuration of a reference image DB 118. The reference image DB 118 is stored in the memory such as the HDD 117 or the like of the managing device 110, for example. In the reference image DB 118 are stored the inspection item and the reference image in association with each other. As illustrated in FIG. 6, the reference image includes a qualified image and a disqualified image. Here, the qualified image is an image of an inspection target judged as qualified. The disqualified image is an image of an inspection target judged as disqualified. As described above, the reference image DB 118 stores the reference image in a manner to be able to be identified as the qualified image or the disqualified image. Note that the qualified image and the disqualified image are created and registered in the reference image DB 118 in advance by a designer or the like before the actual processing is performed, such as at the time of designing of the AR display system.

The CPU 111 of the managing device 110 extracts the reference image associated with the inspection item in the reference image DB 118. Note that there are a case where both qualified image and disqualified image are stored and a case where only either one of the images is stored, in association with the inspection item. In the case of the former, both qualified image and disqualified image are extracted. In the case of the latter, either one of the qualified image and the disqualified image is extracted.

Next, in S103, the CPU 111 of the managing device 110 transmits the reference image having been extracted and information for identifying whether each reference image is the qualified image or the disqualified image, in association with each other, to the AR display device 100 via the communication I/F 114.

When receiving the reference image in S103, the CPU 101 of the AR display device 100 proceeds the processing to S104. Here, the processing of S103 is an example of a reception processing to receive at least one of the qualified image and the disqualified image. In S104, the CPU 101 of the AR display device 100 extracts one qualified image and one disqualified image from the reference images having been received, and displays the above images on the display unit 105. FIG. 7 is a diagram illustrating a display example of the qualified image and the disqualified image. One qualified image 221 and one disqualified image 223 are displayed on the left side and the right side of the display unit 105, respectively. Thereby, the inspector sees the emblem 201 of the finished car 200 as the inspection target existing in the reality space via the display unit 105, and can simultaneously see the qualified image 221 and the disqualified image 223 which are displayed on the display unit 105. In other words, the inspector can recognize an augmented reality space in which the qualified image 221 and the disqualified image 223 are superimposed on the inspection target existing in the reality space.

Further, in a vicinity of the qualified image 221, letters "OK" are displayed as information 222 indicating that the image is the qualified image, and in a vicinity of the NG image 223, letters "NG" are displayed as information 224 indicating that the image is the disqualified image. Note that the information indicating that the image is the qualified image or the disqualified image is preferable to be what the inspector of multiple nations can comprehend easily. For example, the information may be symbols such as a circle and a cross.

Further, the AR display device 100 is preferable to display the qualified image and the disqualified image in the display unit 105 at predetermined display positions, respectively. Thereby, the inspector can specify whether the image is the qualified image or the disqualified image based on the display position, without checking the information 222, 224 which indicates whether the image is the qualified image or the disqualified image. The AR display device 100 according to this embodiment displays the qualified image on the left side of the display unit 105 and displays the disqualified image on the right side of the display unit 105. Further, if receiving only one of the qualified image and the disqualified image in S103, the CPU 101 of the AR display device 100 displays only the received image (qualified image or disqualified image) in S104.

The CPU 101 of the AR display device 100 displays "⅓" adjacently to the qualified image 221. Here, a denominator "3" is the total number of the qualified images received in S103, and a numerator "1" is an identification number of the qualified image 221 which is being displayed. Further, the CPU 101 of the AR display device 100 similarly displays "¼" adjacently to the disqualified image 222.

Further, the CPU 101 of the AR display device 100 can switch the image to display on the display unit 105, in response to an instruction from the inspector. For example, when the inspector speaks "change the qualified image", the CPU 101 of the AR display device 100 accepts a display switching instruction of the qualified image. Then, in place of the qualified image which is being displayed, the CPU 101 of the AR display device 100 displays another qualified image which having been received. Similarly, when the inspector speaks "change the disqualified image", the CPU 101 of the AR display device 100 accepts a display switching instruction of the disqualified image, and in place of the disqualified image which is being displayed, displays another disqualified image having been received. As described above, the CPU 101 of the AR display device 100 switches the display image every time the display switching instruction is accepted, so that the qualified images and the disqualified images which have been received can be displayed in sequence. Here, the processing of S104 is an example of a display processing to display the image received from the managing device 110.

Note that the number of the images displayed simultaneously on the display unit 105 should not be limited to the embodiment. As another example, three qualified images and three disqualified images may be displayed on the left side and the right side of the display unit 105 respectively, and in place of the three images which are being displayed, next three images may be displayed every time the display switching instruction is accepted.

Though it is described that the CPU 101 of the AR display device 100 displays the reference image received from the managing device 110 at an opportunity of receiving the reference image in S103, the opportunity is not limited to the above. As another example, the CPU 101 of the AR display device 100 may display the reference image when receiving a reference image in S103 as well as accepting a display instruction of the reference image from the inspector.

The inspector makes the qualified image and the disqualified image displayed on the display unit 105 as described above, and compares the images being displayed and the inspection target existing in the reality space. Then, in a case where the image bearing resemblance exists, the inspector inputs a selection instruction of the image bearing resemblance. For example, if the inspector wants to compare the inspection target with the qualified image which is being displayed, the inspector speaks "select the qualified image". On this occasion, the CPU 101 of the AR display device 100 performs a voice recognition processing to the voice having been input to the microphone 106, and in response to a recognition result, determines that the selection instruction of the qualified image which is being displayed is accepted. Similarly, the CPU 101 of the AR display device 100 can accept a selection instruction of the disqualified image which is being displayed.

In response thereto, in S105, if accepting the selection instruction (Yes in S105), the CPU 101 of the AR display device 100 proceeds the processing to S106. If not accepting the selection instruction (No in S105), the CPU 101 of the AR display device 100 proceeds the processing to S114. Here, the processing of S105 is an example of an accepting processing to accept the selection instruction of one image of the images which are being displayed by the display unit 105.

In S106, the CPU 101 of the AR display device 100 displays the image (qualified image or disqualified image) related to the selection instruction while enlarging the image, and thereafter, proceeds the processing to S107.

Figure 8A:
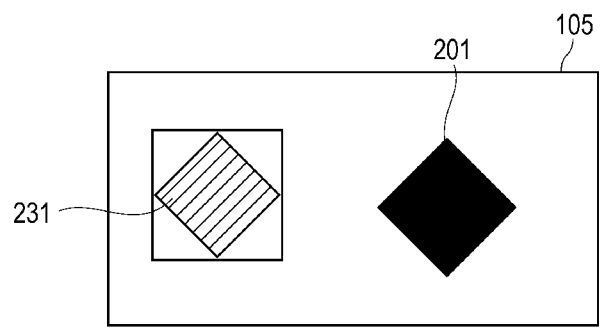
FIG. 8A is a diagram illustrating an enlarged display example of an image related to a selection instruction.
Figure 8B:
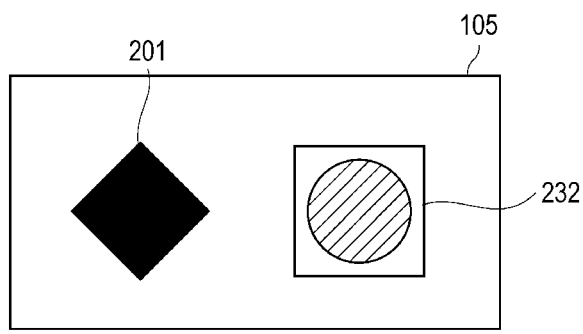
FIG. 8B is a diagram illustrating an enlarged display example of an image related to a selection instruction.

FIG. 8A is a diagram illustrating an enlarged display example of a qualified image. The qualified image 231 is displayed on the left side of the display unit 105. Further, FIG. 8B is a diagram illustrating an enlarged display example of a disqualified image. The disqualified image 232 is displayed on the right side of the display unit 105. The CPU 101 of the AR display device 100 further accepts a magnification change instruction from the inspector, and can enlarge or reduce the qualified image 231 or the disqualified image 232 in response to the magnification change instruction. Thereby, it is possible to adjust a display size of the qualified image 231 and the disqualified image 232 to a size the same as a size which the inspector visually recognizes, as for the inspection target 201 in the reality space, for example. Further, by moving a line of sight, the inspector can make the qualified image 231 or the disqualified image 232 displayed beside the inspection target 201. Further, the CPU 101 of the AR display device 100 can change a display position of the qualified image 231 or the disqualified image 232, in accordance with an instruction from the inspector. Thereby, similarly to the above, it is possible to make the qualified image 231 or the disqualified image 232 displayed beside the inspection target 201. As described above, the inspector can compare the actual inspection target and the qualified image 231 or the disqualified image 232 without moving the line of sight, which enables more accurate judgment of qualified or disqualified.

However, there is a case where judgment of qualified or disqualified is difficult even if the inspector refers to the displayed image, such as a case where the inspection target is dissimilar to all the qualified image and disqualified image which are displayed on the display unit 105. In such a case, the inspector speaks "request judgment", for example. In response thereto, the CPU 101 of the AR display device 100 performs a voice recognition processing to the inspector's voice having been input to the microphone 106, and from a recognition result, determines that a judgment request instruction is accepted.

In response thereto, in S107, the CPU 101 of the AR display device 100 confirms whether or not the judgment request instruction is accepted. If accepting the judgment request instruction (Yes in S107), the CPU 101 of the AR display device 100 proceeds the processing to S108. If not accepting the judgment request instruction (No in S107), the CPU 101 of the AR display device 100 proceeds the processing to S116. Here, the processing of S107 is an example of an accepting processing to accept the judgment request instruction. In S108, the CPU 101 of the AR display device 100 performs a photographing control processing. This processing is a processing to photograph an image and store the image in the memory, similarly to the photographing control processing in S106. Next, in S109, the CPU 101 of the AR display device 100 transmits a photographed image obtained in S108 to the PC 120, while associating the photographed image with the inspection item selected in S100. As another example, in S109, the CPU 101 of the AR display device 100 may transmit a photographed image obtained in S106. In this case, the processing of S108 can be omitted.

In S109, when receiving the photographed image and the inspection item, the CPU 111 of the PC 120 proceeds the processing to S110. In S110, the CPU 111 of the PC 120 displays the received photographed image together with the inspection item, on the display unit 115. On this occasion, a supervisor or the like of the inspector, the supervisor or the like being a user of the PC 120, checks the photographed image displayed on the display unit 115, judges as qualified or disqualified, and inputs a judgment result via the input unit 116. Here, it suffices that the PC 120 is a device used by a predetermined person who can make correct determination to the inspection. As another example, the PC 120 may be a device used by a manager of a criterion in an inspection process, a manager of an entire final inspection process, or the like.

In response to the processing of the PC 120, in S111, the CPU 111 of the PC 120 accepts an input of the judgement result. Next, in S112, the CPU 111 of the PC 120 transmits the judgment result to the AR display device 100 via the communication I/F 114. In response thereto, in S112, when receiving the judgment result, the CPU 101 of the AR display device 100 proceeds the processing to S113. In S113, the CPU 101 of the AR display device 100 displays the judgment result on the display unit 105. Thereby, the inspector can obtain a correct inspection result speedily also to an inspection target for which the inspector himself cannot make determination. Note that the CPU 101 of the AR display device 100 ends display of the judgment result appropriately, in accordance with an instruction from the inspector.

Next, in S114, the CPU 101 of the AR display device 100 transmits an image registration instruction of the photographed image obtained in S108 to the managing device 110, and thereafter proceeds the processing to S116. Here, the image registration instruction includes the inspection item and the judgment result which is received in S112, in addition to the photographed image. When receiving the image registration instruction, the CPU 111 of the managing device 110 proceeds the processing to S115. In S115, the CPU 111 of the managing device 110 registers the photographed image related to the image registration instruction, in association with the inspection item related to the image registration instruction, in the reference image DB 118.

Incidentally, as another example, in a case of receiving the judgment result as well as accepting the image registration instruction from the inspector, the CPU 101 of the AR display device 100 may execute the processings of S114 and S115, to thereby register the image.

Further, in S116, the CPU 101 of the AR display device 100 accepts the judgment result which is input by the inspector. Next, in S117, the CPU 101 of the AR display device 100 transmits the judgment result to the managing device 110. When receiving the judgment result, in S118, the managing device 110 stores the judgment result in association with the inspection item. Next, in S118, the managing device 110 stores the judgment result in the memory such as the HDD 117.

Incidentally, in a case where the AR display device 100 has transmitted the photographed image in S114, the AR display device 100 transmits identification information of the photographed image which has been transmitted in S114 together with the judgment result. When receiving the identification information and the judgment result, the managing device 110 specifies the photographed image to be identified by the identification information, in the reference image DB 118. Then, the managing device 110 stores the judgment result, that is, information indicating that the image is the qualified image or the disqualified image, in the reference image DB 118, in association with the photographed image having been specified.

After the processing of S117, in S119, in response to speech by the user, the CPU 101 of the AR display device 100 confirms whether or not a display end instruction of the reference image is accepted. If not accepting the display end instruction (No in S119), the CPU 101 of the AR display device 100 proceeds the processing to S104. As another example, if not accepting the display end instruction (No in S119), the CPU 101 of the AR display device 100 may proceed the processing to S101. Thereby, it is possible to refer to the reference image DB 118 in a newer state. Meanwhile, if accepting the display end instruction (Yes in S119), the CPU 101 of the AR display device 100 ends the processing.

As described above, the AR display device 100 according to this embodiment displays the qualified image and the disqualified image superimposed on the inspection target existing in the reality space. Thus, in performing judgment of the inspection target, the inspector can judge whether the inspection target is qualified or disqualified while looking at the images of actual qualified product and disqualified product. As described above, in the inspection process using the AR display system according to this embodiment, it is possible to use the images (qualified image and disqualified image) as the criteria for the inspection, instead of letters which may include ambiguity regarding judgment of qualified or disqualified. Thus, the inspector can perform judgement (inspection) of the inspection target more easily and accurately. As described above, the AR display system according to this embodiment can perform support leading to improvement of the inspection accuracy of the visual inspection by the inspector.

Besides, when an inspector is not certain about judgment of qualified or disqualified, the inspector conventionally judged by his subjectivity and input a result, sometimes leading to a case where appropriate judgment was not made. Even in such a case, a criterion of the inspection is not necessarily updated, resulting in that inappropriate judgment is sometimes repeated in inspecting a similar inspection object next time. In contrast, in the inspection process using the AR display system according to this embodiment, it becomes possible to update the criterion promptly. Therefore, in inspecting a similar inspection object next time, the inspector can make judgment based on an objective criterion, which can prevent repetition of the inappropriate judgment. Besides, in a case of updating a criterion of an inspection, a manager or the like was required to rewrite the criterion described in a manual by hand. Further, in a case where the same inspection is performed in factories in a plurality of nations, translation to languages of respective nations was necessary. In contrast, as described above, in the inspection process using the AR display system according to this embodiment, the reference image is used as the criterion and new reference images are automatically accumulated, whereby the criterion is updated. Further, as for the qualified image and the disqualified image to be displayed, the identification information for discriminating both can be displayed by symbols or letters common in multiple nations, such as a circle and a cross. Therefore, it is possible to eliminate necessity of updating a criterion by hand by a manager or the like, and further, to eliminate necessity of translation at the time of update.

Next, a first modification example of the AR display system according to this embodiment will be described. In view of freedom of both hands, an AR display device 100 is preferable to be a wearable device such as the glass-type device described in this embodiment or a head mount-type device as a head mount display. However, the AR display device 100 is not limited to the wearable one. For example, in a case where moving a line of sight at the time of inspection is rare, the AR display device 100 may be equipped at a position in a direction of the line of sight of an inspector as well as at a position between the inspector and an inspection target, to display the inspection target transparently, for example. Further, as another example, the AR display device 100 may be a portable one.

Further, as a second modification example, an AR display device 100 is not limited to an optical see-through displayer. As another example, the AR display device 100 may be a video see-through displayer. In this case, at a time of starting a processing illustrated in FIG. 5, a CPU 101 of the AR display device 100 controls a photographing unit 107 to photograph an image of an inspection target, and displays a video picture of a reality space as a photographed image, on a display unit 105. Then, in S104, the CPU 101 of the AR display device 100 superimposingly displays a qualified image and a disqualified image superimposed on the video picture of the inspection target of the reality space, the video picture being displayed on the display unit 105. Further, in S106, the CPU 101 of the AR display device 100 displays, in place of the inspection target of the reality space, an image related to a superimpose-displaying instruction superimposed on the image of the inspection target in the video picture of the reality space which is being displayed on the display unit 195.

A third modification example will be described. The AR display device 100 according to this embodiment is one which displays a 2D image, but an AR display device may be one which displays a 3D image, instead. In this case, it suffices that the AR display device 100 has two display units at positions corresponding to a right eye and a left eye and displays images enabling the 3D image on respective display units.

Further, as a fourth modification example, an AR display device 100 may store reference images corresponding to all inspection items that may be executed, in a memory such as a ROM 102, in advance. Then, when accepting a selection instruction of the inspection item in S100 illustrated in FIG. 5, in S104, the AR display device 100 reads a reference image related to the selection instruction from the reference images stored in the memory (reading processing), and displays the reference image having been read. In other words, in this case, processings of S101 to S103 are unnecessary. Further, the AR display device 100 may periodically transmit an image acquisition request for updating to a managing device 110, receive a reference image for updating (reference image for adding) from the managing device 110, and store the reference image in the memory.

Note that in order to specify a reference image having been transmitted previously, the AR display device 100 stores a reception date and time every time the reference image is received, and transmits an image acquisition request for updating which includes information of previous reception date and time, for example. Further, as another example, it is possible to store a transmission date and time when a managing device 110 transmits the reference image for updating to the AR display device 100.

Note that a timing when the AR display device 100 receives the reference image for alteration should not be particularly limited. As another example, the AR display device 100 may receive the reference image for updating at a timing when the selection instruction is accepted in S100 of FIG. 5.

Further, as a fifth modification example, an AR display device 100 may proceed an inspection automatically, instead of proceeding the inspection in response to an input of a selection instruction of an inspection item from an inspector (S100 of FIG. 5). For example, the AR display device 100 stores inspection information corresponding to a specification sheet, in an HDD 117 or the like, in advance. Here, the inspection information is information indicating the inspection item and an inspection order of the respective inspection items.

Then, the inspector inputs an instruction of inspection start, at an inspection start time. In response thereto, the AR display device 100 specifies the first inspection item listed in the inspection information and transmits an acquisition request of an image which includes the first inspection item to the managing device 110, to thereby receive a reference image of the first inspection item, and then displays the reference image. Thereafter, at the time that the first inspection has ended, the inspector inputs an instruction of inspection end. When accepting the instruction of inspection end, the AR display device 100 proceeds an inspection object to the next inspection item, while referring to the inspection information. Then, the AR display device 100 transmits an acquisition request of an image which includes the second inspection item to the managing device 110, to thereby receive a reference image corresponding thereto, and displays the reference image. It is only necessary that similar processings be repeated.

Figure 9:
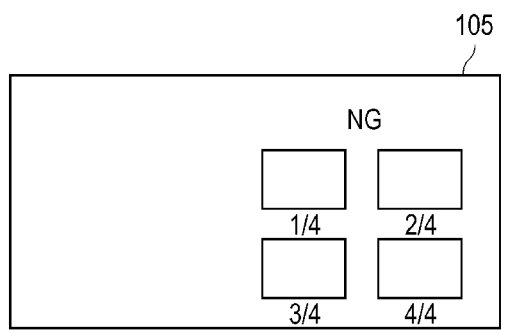
FIG. 9 is a diagram illustrating a display example of a reference image.

Further, as a sixth modification example, an AR display device 100 is not limited to the embodiment in terms of disposition of a reference image at the time that the reference image is displayed on a display unit 105 in S104 of FIG. 5. For example, the AR display device 100 may display a plurality of disqualified images on the right side of the display unit 105, as illustrated in FIG. 9. Further, as another example, in S104, only a qualified image 231 or only a disqualified image 232 may be displayed on the display unit 105, as illustrated in FIG. 8A and FIG. 8B. Note that also in this case, the total number and an identification number of an image which is being displayed may be displayed in a form of fraction, similarly to the case described with reference to FIG. 7.

Further, as a seventh modification example, in S106 of FIG. 5, an AR display device 100 may perform size adjustment and a display position adjustment of an image related to a selection instruction automatically, without accepting an instruction from an inspector. More specifically, a CPU 101 of the AR display device 100 first controls a photographing unit 107, to thereby acquire a photographed image. Then, the CPU 101 performs image recognition to the photographed image, extracts an image of an inspection target (image recognition processing), and specifies a position and a size in the image of the inspection target in the photographed image. The CPU 101 of the AR display device 100 further decides a display position and a display size of the image related to the selection instruction, based on a relationship between a photographing direction and a sight line direction and the position and the size of the inspection target in the photographed image.

Here, the display position is a position adjacent to the inspection target. The CPU 101 of the AR display device 100 displays the image related to the selection instruction at the decided display position with the decided display size. Here, the adjacent position is a position making a distance between a position grasped by the inspector of the inspection target in the display unit 105 and the aforementioned display position be of a predetermined length, and further preferably, a position making the inspection target and the image not overlap each other. Further, the adjacent position may be a position decided in correspondence with the size grasped by the inspector of the inspection target in the display unit 105.

Further, as an eighth modification example, images which an AR display device 100 displays as a qualified image and a disqualified image are not limited to still images and may be moving images. Further, as another example, the AR display device 100 may create an animation from a moving image photographed by a photographing unit 107 and display the animation as a qualified image and a disqualified image.

Further, as a ninth modification example, an AR display device 100 may register, not only a photographed image of a judgment result received from a PC 120, but also a photographed image which an inspector desires to register in a reference image DB 118 as a reference image, in association with a judgment result, in the reference image DB 118.

Further, as a tenth modification example, an AR display device 100 may photograph and store an image of an inspection target during an inspection or at an inspection end time, as for all inspection items, not only for a case where judgement is difficult for an inspector. Thereby, if a defect or the like occurs later, a cause of the defect can be found out. For example, the AR display device 100 stores the photographed image in a managing device 110 as an inspected image, other than a reference image. Further, the AR display device 100 may store an inspection result in association with the inspected image.

Further, as an eleventh modification example, an inspection object is not limited to an emblem of an automobile, and may be a woodgrain steering wheel, a space between a back door and a body, a caution label, an ornament, and so on, for example. Further, the inspection object is not limited to a finished car inspection, but application to a completion inspection in an assembling process or a painting process of an automobile is possible. Further, as another example, application to an inspection of a building, an inspection of a plant/equipment/device, and so on is possible.

Hereinabove, according to each embodiment described above, it is possible to perform support which leads to improvement of an inspection accuracy of a visual inspection by an inspector.

Hereinabove, preferred embodiments of the present invention have been described in detail, but the present invention should not be limited to the specific embodiments and various alternation and modification are possible within a range of the scope of the present invention that is disclosed in the claims.

The invention claimed is:
1. A display system comprising:
a display device configured to be able to display an image superimposed on a reality space; and
a managing device configured to manage the image the display device displays,
wherein the display device comprises:
a reader configured to read at least one of a qualified image and a disqualified image for an inspection target existing in the reality space, from a memory;

a display processor configured to display the read image superimposed on the reality space seen through an optical see-through displayer, on the displayer;

an acceptor configured to accept a selection instruction of one image of the images the display processor is displaying;

a photographing controller configured to control photographing of the inspection target existing in the reality space, when accepting the selection instruction; and an image recognizer configured to extract the image of the inspection target, by an image recognition processing for a photographed image obtained by control of the photographing controller, and wherein the display processor displays the image related to the selection instruction at a position adjacent to the inspection target in the reality space, based on a position of the inspection target which is obtained by the image recognizer.

2. The display system according to claim 1, wherein the display device is a wearable device.

3. The display system according to claim 1, wherein the display device is a portable device.

4. A display system comprising:
a display device configured to be able to display an image superimposed on a reality space; and
a managing device configured to manage the image the display device displays,
wherein the display device comprises:
  a reader configured to read at least one of a qualified image and a disqualified image for an inspection target existing in the reality space, from a memory;
  a display processor configured to display the read image superimposed on the reality space seen through an optical see-through displayer, on the displayer;
  an acceptor configured to accept a judgment request instruction of the inspection target of the reality space;
  a photographing controller configured to control photographing of the inspection target, when accepting the judgment request instruction;
  a first transmitter configured to transmit a photographed image obtained by control of the photographing controller to an external device; and
  a receiver configured to receive a judgment result of qualified or disqualified for the photographed image from the external device; and
  a second transmitter configured to transmit the photographed image together with the judgment result, to the managing device, and
wherein the managing, device comprises:
  a register configured to register the photographed image in association with the judgment result, in the memory; and
  a transmitter configured to transmit the photographed image registered in the memory to the display device, as the qualified image or the disqualified image, in accordance with the judgment result; and
wherein the display processor is configured to display the judgment result.

5. The display system according to claim 4, wherein the display device is a wearable device.

6. The display system according to claim 4, wherein the display device is a portable device.

7. A display device capable of displaying an image superimposed on a reality space, the display device comprising:
  a reader configured to read at least one of a qualified image and a disqualified image for an inspection target existing in the reality space, from a memory; and
  display processor configured to display the read image superimposed on the reality space seen through an optical see-through displayer, on the displayer,
  wherein the display device further comprises:
    an acceptor configured to accept a selection instruction of one image of the images the display processor is displaying;
    a photographing controller configured to control photographing of the inspection target existing in the reality space, when accepting the selection instruction; and
    an image recognizer configured to extract the image of the inspection target, by an image recognition processing for a photographed image obtained by control of the photographing controller, and
  wherein the display processor displays the image related to the selection instruction at a position adjacent to the inspection target in the reality space, based on a position of the inspection target which is obtained by the image recognizer.

8. A display method executed by a display system which has a display device capable of displaying an image superimposed on a reality space and a managing device managing the image the display device displays, the display method comprising:
  a reading step configured for the display device to read at least one of a qualified image and a disqualified image for an inspection target existing in the reality space, from a memory;
  a display processing step configured for the display device display the read image superimposed on the reality space seen through an optical see-through displayer, on the displayer;
  an accepting step configured for the display device to accept a selection instruction of one image of the images displayed at the display processing step;
  a photographing controlling step configured for the display device to control photographing of the inspection target existing in the reality space, when accepting the selection instruction; and
  an image recognizing step configured for the display device to extract the image of the inspection target, by an image recognition processing for a photographed image obtained at the photographing controlling step, and
  wherein the image related to the selection instruction is displayed at a position adjacent to the inspection target in the reality space, based on a position of the inspection target which is obtained at the image recognizing step.

9. A display method executed by a display device capable of displaying an image superimposed on a reality space, the display method comprising:
  a reading step configured for the display device to read at least one of a qualified image and a disqualified image for an inspection target existing in the reality space, from a memory;
  a display processing step configured for the display device to display the read image superimposed on the reality space seen through an optical see-through displayer, on the displayer;

an accepting step configured for the display device to accept a selection instruction of one image of the images displayed at the display processing step;

a photographing controlling step configured for the display device to control photographing of the inspection target existing in the reality space, when accepting the selection instruction; and an image recognizing step configured for the display device to extract the image of the inspection target, by an image recognition processing for a photographed image obtained at the photographing controlling step, and wherein the image related to the selection instruction is displayed at a position adjacent to the inspection target in the reality space, based on a position of the inspection target which is obtained at the image recognizing step.

10. A non-transitory computer readable recording medium with a program causing a computer to function as:

a reader configured to read at least one of a qualified image and a disqualified image for an inspection target existing in a reality space, from a memory; and a display processor configured to display the read image superimposed on the reality space seen through an optical see-through displayer, on the displayer, and wherein the displayer further comprises:

an acceptor configured to accept a selection instruction of one image of the images the display processor is displaying;

a photographing controller configured to control photographing of the inspection target existing in the reality space, when accepting the selection instruction; and an image recognizer configured to extract the image of the inspection target, by an image recognition processing for a photographed image obtained by control of the photographing controller, and wherein the display processor displays the image related to the selection instruction at a position adjacent to the inspection target in the reality space, based on a position of the inspection target which is obtained by the image recognizes.

11. A display method executed by a display system which has a display device capable of displaying an image superimposed on a reality space and a managing device managing the image the display device displays, the display method comprising:

a reading step configured for the display device to read at least one of a qualified image and a disqualified image for an inspection target existing in the reality space, from a memory;

a display processing step configured for the display device to display the read image superimposed on the reality space seen through an optical see-through displayer, on the displayer;

an accepting step configured for the display device to accept a selection instruction of one image of the images displayed at the display processing step;

a photographing controlling step configured for the display device to control photographing of the inspection target existing in the reality space, when accepting the selection instruction;

a first transmitting step configured for the display device to transmit a photographed image obtained by control of the photographing controller to an external device;

a receiving step configured for the display device to receive a judgment result of qualified or disqualified for the photographed image from the external device;

a second transmitting step configured for the display device to transmit the photographed image together with the judgment result, to the managing device;

a registering step configured for the display device to register the photographed image in association with the judgment result, in the memory; and a third transmitting step configured for the display device to transmit the photographed image registered in the memory to the display device, as the qualified image or the disqualified image, in accordance with the judgment result, and wherein the judgment result is displayed on the displayer.

* * * * *